(12) United States Patent
Miyahara

(10) Patent No.: US 7,634,330 B2
(45) Date of Patent: Dec. 15, 2009

(54) TEMPERATURE CONTROLLING METHOD AND TEMPERATURE CONTROLLER

(75) Inventor: Seiichiro Miyahara, Tsukuba (JP)

(73) Assignee: Daikin Industries, Ltd., Osaka (JP)

( * ) Notice: Subject to any disclaimer, the term of this patent is extended or adjusted under 35 U.S.C. 154(b) by 236 days.

(21) Appl. No.: 11/569,772

(22) PCT Filed: Apr. 8, 2005

(86) PCT No.: PCT/JP2005/006955

§ 371 (c)(1),
(2), (4) Date: Nov. 29, 2006

(87) PCT Pub. No.: WO2005/118774

PCT Pub. Date: Dec. 15, 2005

(65) Prior Publication Data

US 2008/0234874 A1    Sep. 25, 2008

(30) Foreign Application Priority Data

Jun. 3, 2004    (JP)    ............... 2004-165761

(51) Int. Cl.
*G05D 23/00*    (2006.01)
*C12M 1/00*    (2006.01)
*F27B 1/26*    (2006.01)
*F27D 15/02*    (2006.01)

(52) U.S. Cl. .................... 700/299; 700/300; 435/289.1; 432/36; 432/77

(58) Field of Classification Search ................. 700/299, 700/300; 435/289, 290, 289.1; 432/36, 77
See application file for complete search history.

(56) References Cited

U.S. PATENT DOCUMENTS 5,123,477 A    6/1992    Tyler
5,129,233 A    7/1992    Takegawa et al.

(Continued)

FOREIGN PATENT DOCUMENTS

DE    199 25 154 A1    12/1999

(Continued)

OTHER PUBLICATIONS

"Food Bacteria Inspection System DOX-60F/30F"; 2000-2003 Daikin Environmental Laboratory, Ltd. Presented at Convention for 2000 Japan Society for Bioscience, Biotechnology, and Agrochemistry.

*Primary Examiner*—Ronald D Hartman, Jr.
(74) *Attorney, Agent, or Firm*—Global IP Counselors

(57) ABSTRACT

An object of the present invention is to accurately control temperatures of microorganisms or the like. In the present invention, a temperature controller comprises a plurality of cells for storing microorganisms or the like, heaters, and a cooling section. The heaters selectively heat the plurality of cells, and the cooling section wholly cools the plurality of cells. When the maximum value of temperature of a plurality of places is not lower than a first lower limit, the cooling section is driven. When a temperature of one place is not higher than a first lower limit, the heater to heat the place is driven. When the maximum value is not higher than a second lower limit, the cooling section is stopped. When a temperature of one place is not lower than a second upper limit, the heater to heat the place is not driven.

10 Claims, 8 Drawing Sheets

U.S. PATENT DOCUMENTS

| | | | |
|---|---|---|---|
| 5,142,969 A * | 9/1992 | Chun | 99/468 |
| 5,299,383 A * | 4/1994 | Takakura et al. | 47/58.1 R |
| 5,459,300 A | 10/1995 | Kasman | |
| 5,723,314 A * | 3/1998 | Prakash | 435/69.1 |
| 5,819,842 A * | 10/1998 | Potter et al. | 165/206 |
| 6,633,785 B1 * | 10/2003 | Kasahara et al. | 700/73 |
| 6,988,546 B1 * | 1/2006 | Ohki | 165/263 |
| 2002/0009803 A1 * | 1/2002 | Vajta | 435/325 |
| 2003/0214994 A1 | 11/2003 | Schicke et al. | |
| 2004/0033554 A1 * | 2/2004 | Powers | 435/29 |
| 2004/0239040 A1 * | 12/2004 | Burdgick | 277/414 |
| 2005/0034367 A1 * | 2/2005 | Morrow et al. | 47/65.5 |
| 2005/0081441 A1 * | 4/2005 | Mantovani | 47/67 |

FOREIGN PATENT DOCUMENTS

| | | |
|---|---|---|
| EP | 0 400 829 A1 | 12/1990 |
| FR | 2 692 345 A1 | 12/1993 |
| JP | H07-274938 | 10/1995 |
| JP | H09-122507 | 5/1997 |
| JP | 2003-061641 A | 3/2003 |
| JP | 2003-235544 | 8/2003 |

* cited by examiner

F I G. 1
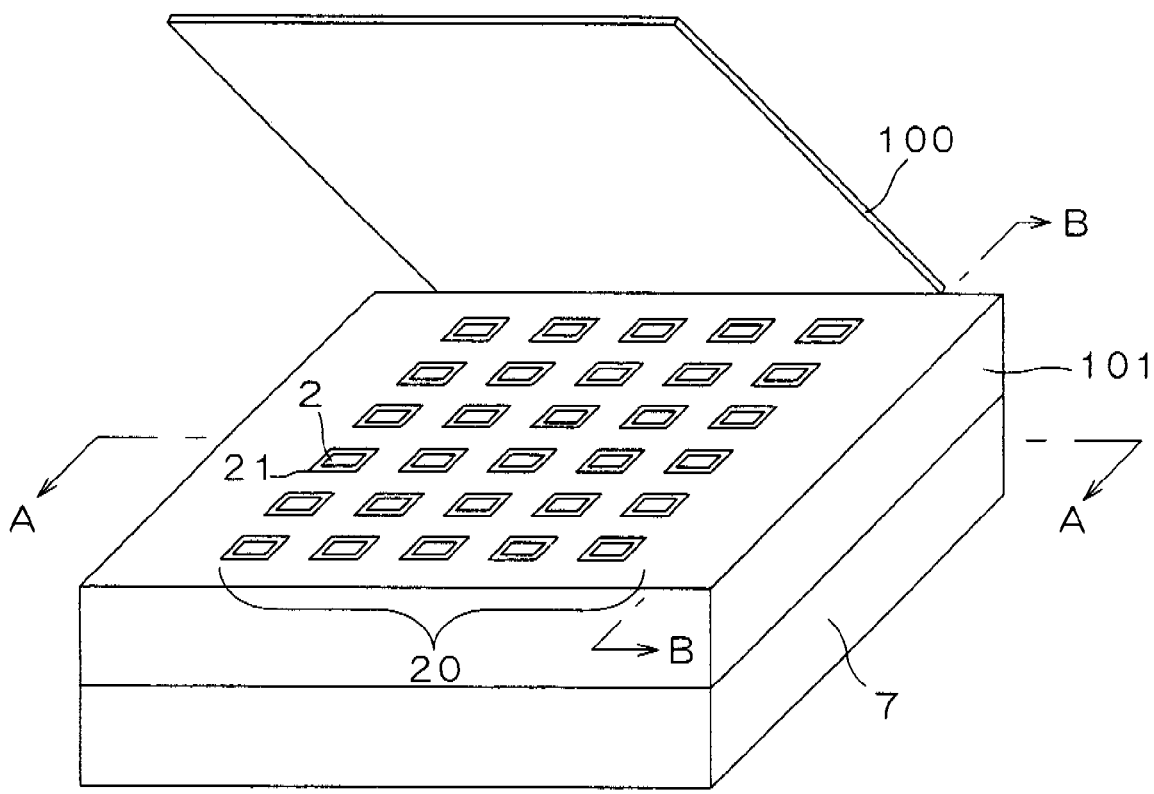

TEMPERATURE CONTROLLING METHOD AND TEMPERATURE CONTROLLER

CROSS-REFERENCE TO RELATED APPLICATIONS

This U.S. National stage application claims priority under 35 U.S.C. 119(a) to Japanese Patent Application No. 2004-165761, filed in Japan on Jun. 3, 2004, the entire contents of which are hereby incorporated herein by reference.

TECHNICAL FIELD

The present invention relates to a temperature controller and can, for example, be applied to culture of microorganisms or cells (hereinafter referred to as "microorganisms or the like").

BACKGROUND ART

The culture speed of microorganisms or the like is sensitive to a temperature of a container (hereinafter referred to as "cell") that houses those (such a temperature is hereinafter referred to as "cell temperature"). It is therefore desirable to accurately control the cell temperature in culture of microorganisms or the like.

On the other hand, there may be cases where microorganisms or the like are desired to be concurrently cultured with the cell temperatures made the same while other conditions varied. As a technique for performing such culture, for example, Non-Patent Document "Food bacteriological examination system DOX-60F/30F (comparison with conventional method). [online] DAIKIN INDUSTRIES, ltd. searched on Mar. 22, 2005, Internet <URL:http//www.del.co.jp/products/dox/sub3.html> exemplifies a technique of using a plurality of cells with different initial values of the number of microorganisms or the like to concurrently culture the microorganisms or the like.

Further, Japanese Patent Laid-Open No. 9-122507 exemplifies a technique of applying a heater and a cooling module for controlling a sample at the optimal temperature in the biotechnology field.

However, the technique described in Japanese Patent Laid-Open No. 9-122507 merely has the heater and the cooling module. The technique therefore has no viewpoint of accurately equating the cell temperatures when microorganisms or the like are concurrently cultured using a plurality of cells under a plurality of different conditions except the cell temperature.

SUMMARY OF THE INVENTION

The present invention was made in view of the foregoing circumstances and has an object to provide a technique of accurately equating temperatures of a plurality of containers.

A first aspect of a temperature controlling method according to the present invention is to control a temperature controller including: a temperature-controlled object (20) whose temperature is to be controlled; heaters (11, 12, . . . , 1n) for heating a plurality of places of the temperature-controlled object; and a cooling section (7) for cooling the whole of the temperature-controlled object. The aspect executes the following steps (a) to (c): (a) a step (S101) of measuring temperatures (T1 to Tn) of the plurality of places; (b) a step (S103, S104) of driving the cooling section when at least one of the temperatures of the places is not lower than a first upper limit (Ts+δ1); and (c) a step (S107, S108) of driving the heater for heating one of the places when the temperature of the one of the places is not higher than a first lower limit (Ts−δ2).

For example, the first upper limit is a value obtained by adding a first positive value (δ1) to a target value (Ts) of a temperature of the object (20) whose temperature is to be controlled, and the first lower limit is a value obtained by subtracting a second positive value (δ2) from the target value.

A second aspect of the temperature controlling method according to the present invention is a temperature controlling method according to the first aspect, and further executes the following steps (d) and (e): (d) a step (S105, S106) of not driving the cooling section when all of the temperatures (T1 to Tn) of the places are not higher than a second lower limit (Ts+δ3); and (e) a step (S109, S110) of not driving the heater for heating one of the places when the temperature of the one of the places is not lower than a second upper limit (Ts+δ4).

For example, the second lower limit is lower than the first upper limit (Ts+δ1), and is a value obtained by adding a third positive value (δ3) to the target value (Ts) of a temperature of the temperature-controlled object (20). Further, the second upper limit is higher than the first lower limit (Ts−δ2), and is a value obtained by adding a fourth positive value (δ4) to the target value.

A third aspect of the temperature controlling method according to the present invention is a temperature controlling method according to the second aspect, and further executes: (f) a step (S800) of calibrating to update the target value (Ts) of a temperature of the object (20) whose temperature is to be controlled to a new target value (Tc) according to an atmospheric temperature (Ta) of the temperature controller when at least one of the temperatures of the places is higher than the second lower limit (Ts+δ3), all of the temperatures (T1 to Tn) of the places are lower than the first upper limit (Ts+δ1), and any of the temperatures of the places is higher than the first lower limit (Ts−δ2) and lower than the second upper limit (Ts+δ4). Then, the steps (b) and (c) are again executed by using the target value updated in the step (f).

It is preferable that the steps (d) and (e) be again executed by using the target value updated in the step (f).

A fourth aspect of the temperature controlling method according to the present invention is a temperature controlling method according to the first to third aspects, and the temperature-controlled object (20) has a plurality of containers (2) capable of housing cultures.

A first aspect of a temperature controller according to the present invention includes: a housing section (101), a cooling section (7), a plurality of heaters (11, 12, . . . 1n), and a plurality of sensors (41, 42, . . . 4n). The housing section houses a plurality of containers (2) whose temperatures are to be controlled. The cooling section concurrently cools all of the plurality containers housed in the housing section. The plurality of heaters heat the plurality of containers. The plurality of sensors measure temperatures of respective places heated by the plurality of heaters.

A second aspect of the temperature controller according to the present invention is a temperature controller according to the first aspect, and further includes a control section (6). The control section controls the drive of the cooling section on the basis of a target value (Ts) of temperatures of the containers. The control section also controls the drive of the heater responsive to the sensor on the basis of each results of temperature measurement by the plurality of sensors.

A third aspect of the temperature controller according to the present invention is a temperature controller according to the second aspect, and further includes a sensor (40) and a calculating section (8). The sensor measures an atmospheric temperature (Ta). The calculating section updates the target value on the basis of the atmospheric temperature and the target value (Ts).

A fourth aspect of the temperature controller according to the present invention is a temperature controller according to the second aspect, and further includes a sensor (40) and a storage section (5). The sensor measures an atmospheric temperature (Ta). The storage section stores calibration data that provides a calibration value (Tc) on the basis of the atmospheric temperature and the target value (Ts). The control section (6) updates the target value with the calibration value on the basis of the calibration data, the atmospheric temperature and the target value.

According to the first aspect of the temperature controlling method according to the present invention, it is possible to enhance the accuracy of a temperature distribution as well as the accuracy of a temperature itself. In particular, since the cooling section cools the whole system, an atmospheric temperature is equivalently decreased in on-off control of the heater even in the case of performing the temperature control at a temperature lower than the atmospheric temperature, which is preferred.

According to the second aspect of the temperature controlling method according to the present invention, excessive cooling and excessive heating are suppressed.

According to the third aspect of the temperature controlling method according to the present invention, since the atmospheric temperature is considered in the temperature control, an effect on the temperature-controlled object, exerted by the atmospheric temperature, can be made small.

According to the fourth aspect of the temperature controlling method according to the present invention, since the temperature control can be performed with accuracy in culture sensitive to temperatures, it is possible to set a temperature condition uniformly for a plurality of cultures.

According to the first aspect of the temperature controller of the present invention, it is possible to execute a temperature control method according to the first to third aspects.

According to the second aspect of the temperature controller of the present invention, it is possible to execute the temperature controlling method according to the first aspect and the second aspect.

According to the third aspect and the fourth aspect of the temperature controller of the present invention, it is possible to execute the temperature controlling method according to the third aspect.

The object, characteristics, aspects and advantages of the present invention are made more apparent by means of the following detailed explanations and attached drawings.

BRIEF DESCRIPTION OF DRAWINGS

FIG. 1 is a conceptual perspective view of a temperature controller according to a first embodiment of the present invention.

DETAILED DESCRIPTION OF THE INVENTION

In the following, a description is made by taking a case as an example where a temperature control technique according to the present invention is applied to culture of microorganisms or the like. However, the temperature control technique according to the present invention is applicable to cases other than the case of culture of microorganisms or the like.

First Embodiment

Figure 2A:
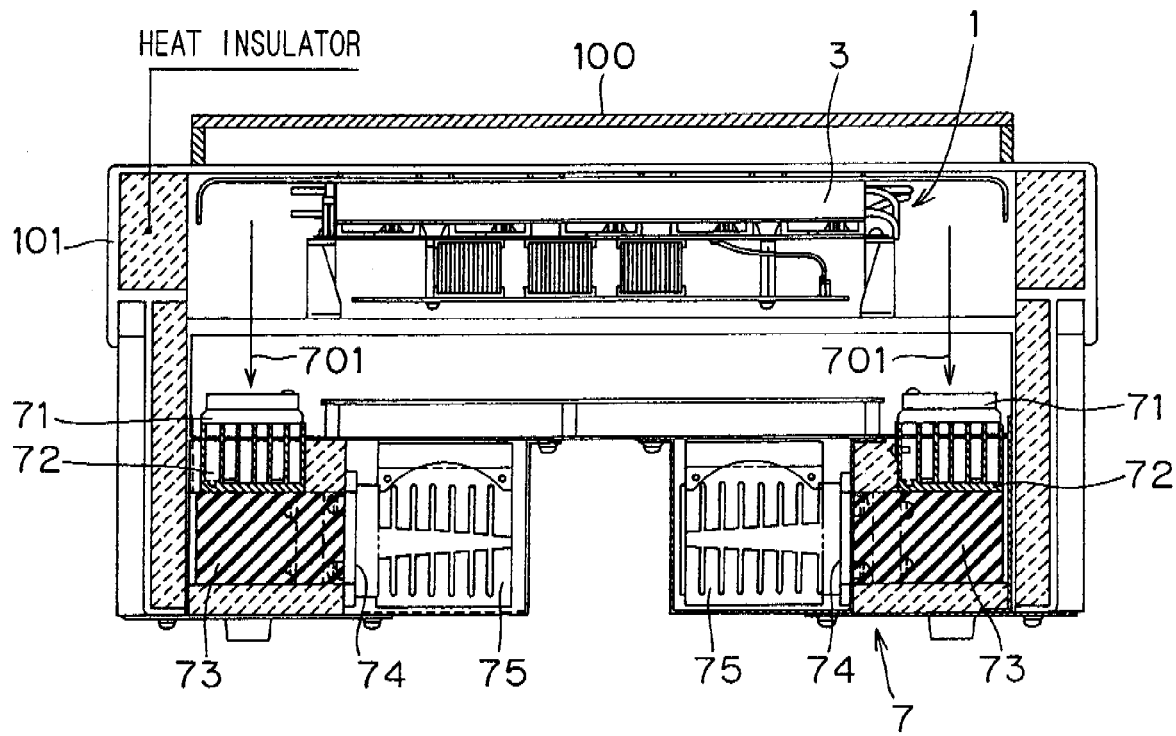
FIGS. 2A and 2B are sectional views at a position AA and a position BB of the temperature controller shown in FIG. 1.
Figure 2B:
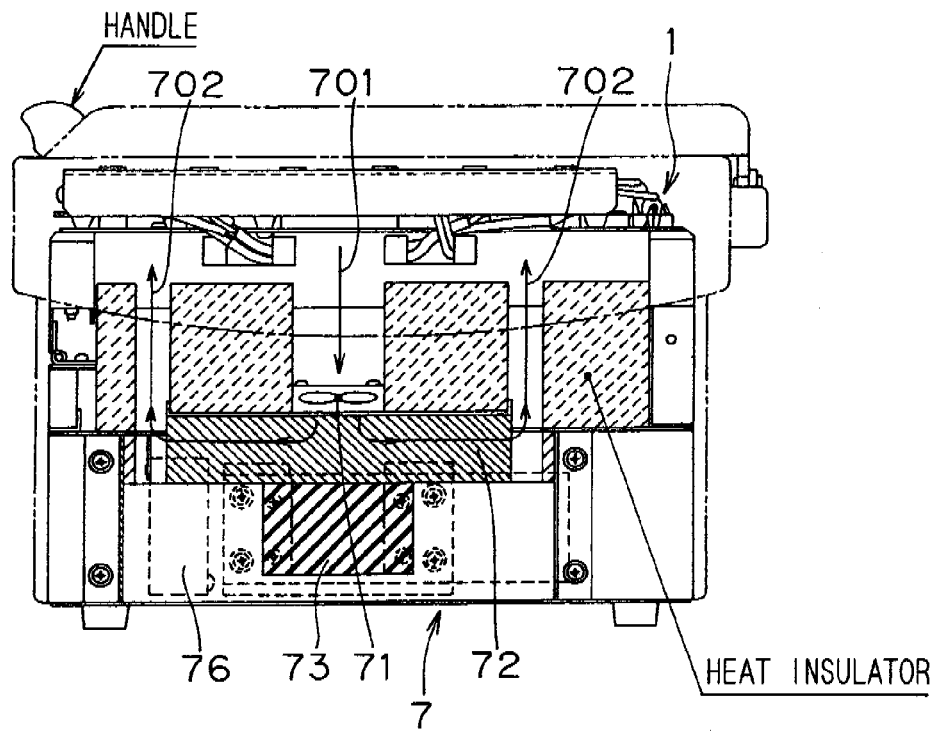

FIG. 1 is a conceptual perspective view of a temperature controller according to the present embodiment. FIGS. 2A and 2B are sectional views at a position AA and a position BB of the temperature controller shown in FIG. 1. The temperature controller includes a cell group 20, a case 101 as a housing section for housing the cell group 20, and a heater group 1 and a cooling section 7 which are both supplied for controlling a cell temperature. The cell group 20 is comprised of a plurality of cells 2 as containers for housing microorganisms or the like.

The case 101 is provided with a plurality of holes 21 for housing the cell group 20. For example, the cell 2 has an opening for pouring microorganisms or the like and a lid for closing the opening. The cells 2 are housed in the holes 21 such that the opening side is located on the surface side of the case 101.

It is to be noted that as shown in FIG. 1, the temperature controller may be provided with the cover 100. It is aimed at preventing foreign materials such as dust from getting in the holes 21.

The heater group 1 is provided in the peripheries of the cells 2. The cooling section 7 has a cooling fan 71, a cooling fin 72, an aluminum conductive block 73, a Peltier device 74, a radiation fin 75, and a radiation fan 76.

The cooling fan 71 sends air in the vicinity of the cell group 20 to the cooling fin 72 along a channel 701. The air cooled by the cooling fin 72 is sent to the vicinity of the cell group 20 along a channel 702. By such circulation and cooling of the air, all of the cells 2 housed in the case 101 are concurrently cooled. Even when the air flows in a direction opposite to the channels 701 and 702, the cell group 20 is cooled.

The heat obtained by the cooling fin 72 is provided to the aluminum conductive block 73. The Peltier device 74 shifts the heat from the aluminum conductive block 73 side to the radiation fin 75 side. The heat shifted to the radiation fin 75 is released to the outside by the radiation fan 76.

Figure 3:
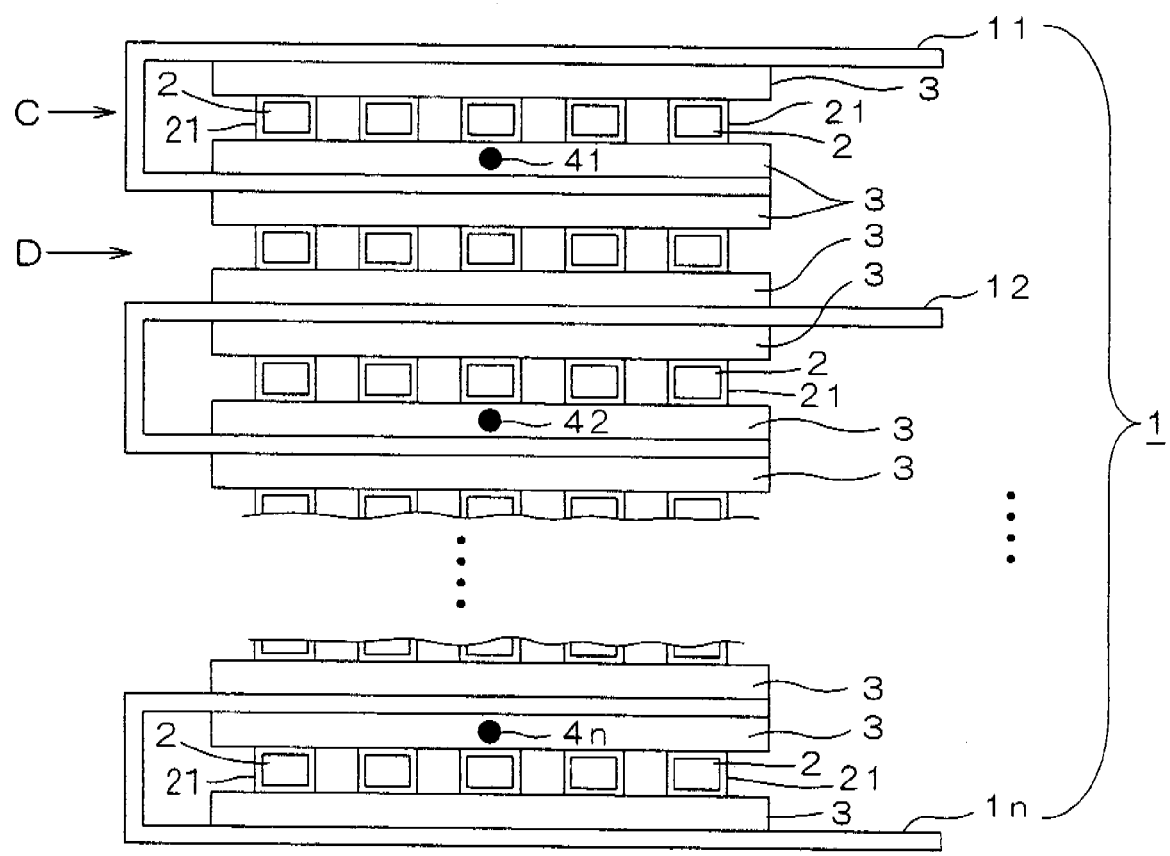
FIG. 3 is a plan view exemplifying a positional relation between holes 21 and a heater group 1.

FIG. 3 is a plan view exemplifying the positional relationship between the holes 21 and the heater group 1. However, the representation of the case 101 itself is omitted for avoiding complexity of the illustration.

The heater group 1 has a plurality of heaters 11, 12, . . . 1n. The cells 2 are housed in the holes 21. The holes 21 are adjacent to one or more heaters through heat blocks 3. This allows selective heating of the cell 2 by the heater group 1.

For example, the holes 21 arranged in a position C in the figure are adjacent to the heater 11 from both sides in a direction orthogonal to the arrangement of the holes 21 via different heat blocks 3. Further, the holes 21 arranged in a position D are adjacent to the heater 11 from one side and adjacent to the heater 12 from the other side in the direction orthogonal to the arrangement via different heat blocks 3.

One of the heat blocks 3 adjacent to the heaters 1$k$ ($k$=1, 2, . . . n) is provided with a sensor 4$k$ for measuring a temperature of a place heated by the heater 1$k$.

Figure 4:
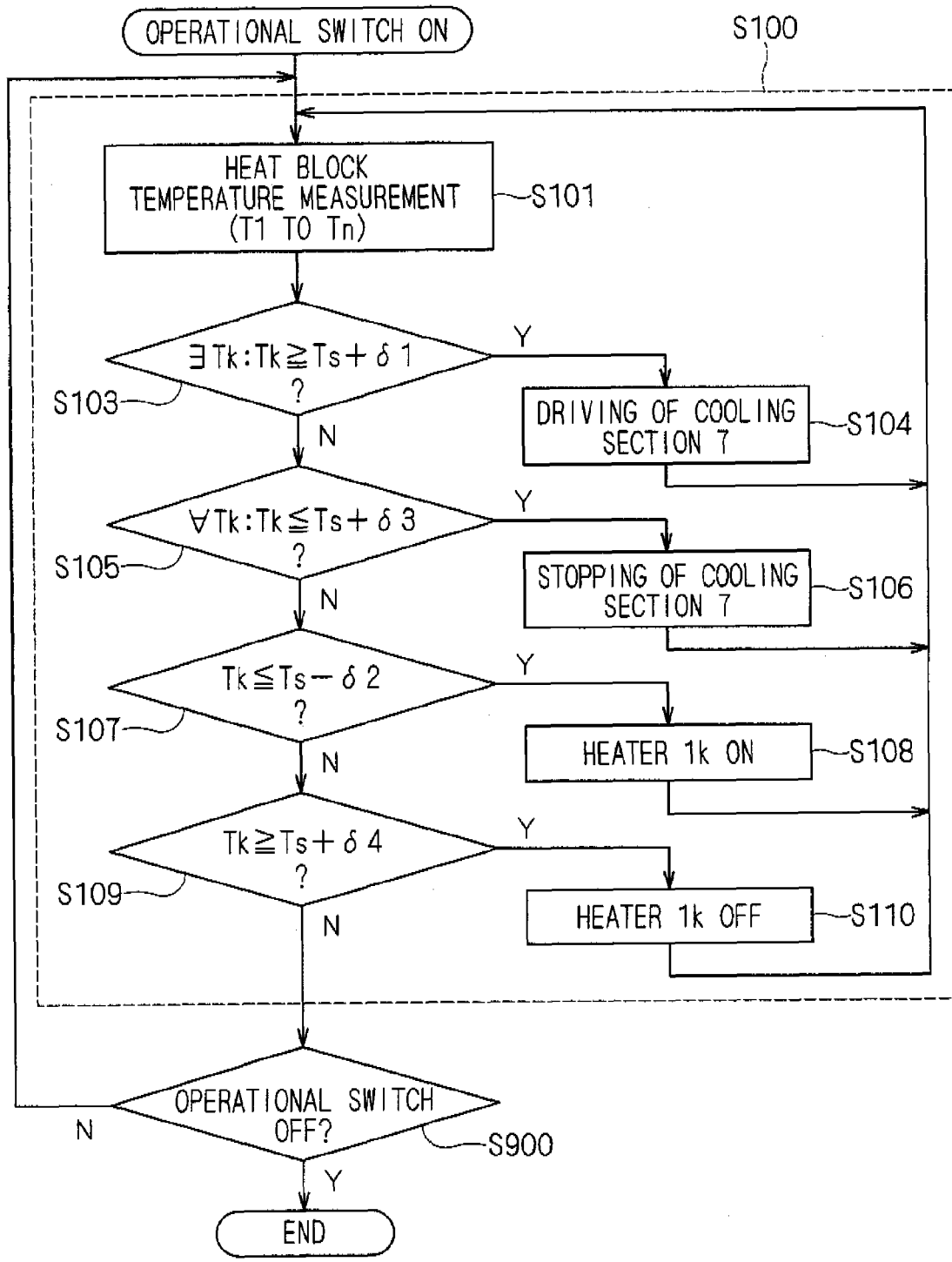
FIG. 4 is a flowchart exemplifying a temperature controlling method according to the first embodiment of the present invention.

FIG. 4 is a flowchart exemplifying a temperature controlling method according to the present embodiment. An object whose temperature is to be controlled is the cell group 20, and more specifically the whole of the cells 2 housed in the case 101. The temperature of the heat block 3 is adopted as the cell temperature. This is because insertion of the censor into the cell 2 in culturing microorganisms or the like inside the cell 2 is not preferred, and the cells 2 housed in the holes 21 adjacent to the heat block 3 are considered to exhibit an almost uniform cell temperature with the temperature of the heat block 3.

As thus described, a plurality of cells 2 are present each as the object whose temperature is to be controlled, and the heaters 11, 12, . . . , 1$n$ selectively heat a plurality of places. On the other hand, the cooling section 7 cools the whole of the objects whose temperatures are to be controlled.

A target value of the cell temperature desired to be set is Ts. This target value is common to all the cells 2. When an operational switch of the temperature controller is turned on, first, in Step S101, temperatures T1 to Tn of a plurality of places heated by the heaters 11, 12, . . . , 1$n$ are measured. Specifically, the temperatures T1 to Tn are measured by censors 41 to 4$n$.

Next, in Step S103, it is determined whether or not at least one of those temperatures Tk is not smaller than a prescribed upper limit (Ts+δ1). In FIG. 4, it is shown using a symbol ∃ that the temperature Tk is present which satisfies a condition represented to the right of a colon, namely a condition of being not smaller than the upper limit (Ts+δ1). Here, for example, δ1 is a positive value and 1° C. is adopted.

When it is determined that at least one cell is present which is responsive to the temperature Tk satisfying the condition of Step S103, the process proceeds to Step S104, and the cooling section 7 is driven. Then returning to Step S101 is done.

When it is determined that all the temperatures Tk do not satisfy the condition of Step S103, the process proceeds to Step S105. It is then determined whether or not all the temperatures Tk are not larger than a prescribed lower limit (Ts+δ3). In FIG. 4, it is shown using a symbol V that all the temperatures Tk satisfy a condition represented to the right of a colon, namely a condition of being not larger than the lower limit (Ts+δ3). Here, δ3 is smaller than δ1, and for example, δ3 is a positive value and 0.5° C. is adopted.

When all the temperatures Tk satisfy the condition of Step S105, it is determined that the cell temperatures of all the cells 2 have excessively decreased with respect to the target value. Therefore, the process proceeds to Step S106, to stop the cooling section 7. The process then returns to Step S101.

When at least one of the temperatures Tk does not satisfy the condition of Step S105, proceeding to Step S107 is done. Then, the individual measured temperatures Tk are compared with a prescribed lower limit (Ts−δ2). Here, for example, δ2 is a positive value and 0.1° C. is adopted.

When one measured temperature Tk is not larger than the lower limit (Ts−δ2), it is determined that the cell 2 adjacent to the heat block 3 where the sensor 4$k$ are arranged has been excessively cooled. Therefore, the heater 1$k$ responsive to the sensor 4$k$ is turned on. Then returning to Step S101 is done.

When any of the measured temperatures T1 to Tn is higher than the lower limit (Ts−δ2), proceeding to Step S109 is done. The individual measured temperatures Tk are compared with a prescribed upper limit (Ts+δ4). Here, δ4 is larger than −δ2, and for example, δ4 is a positive value and 0.1° C. is adopted.

When one measured temperature Tk is not smaller than the upper limit (Ts+δ4), it is determined that the cell 2 adjacent to the heat block 3 where the sensor 4$k$ is arranged has been excessively heated. Therefore, the heater 1$k$ responsive to the sensor 4$k$ is turned off. Then returning to Step S101 is done.

When any of the measured temperatures T1 to Tn is lower than the upper limit (Ts+δ4), proceeding to Step S900 is done. Then returning to Step S101 is done unless the operational switch is turned off. In FIG. 4, Step S100 includes Steps S101 to S109 and return channels from Steps S104, S106, S108 and S110 to Step S101. Therefore, it can be understood that Step S100 is repeated until the determination in Step S900 becomes affirmative.

As thus described, the cooling section 7 is driven (S104) when the temperature Tk not lower than the upper limit (Ts+δ1) is present and the heater 1$k$ is turned on (S108) when one measured temperature Tk is not higher than the lower limit (Ts−δ2), whereby allowing enhancement in accuracy of the temperature distribution as well as accuracy of the temperature itself. In particular, since the cooling section 7 cools all the cells 2 concurrently, an atmospheric temperature is equivalently decreased in on-off control of the heater even in the case of performing the temperature control at a temperature lower than the atmospheric temperature, which is preferred.

Further, the cooling section 7 is not driven (S106) when all the measured temperatures Tk are not larger than the lower limit (Ts+δ3), and the heater 1$k$ is turned off (S110) when one measured temperature Tk is not smaller than the upper limit (Ts+δ4), thereby allowing suppression of excessive cooling or excessive heating of the cell 2.

As thus described, since the use of the temperature control technique according to the present invention allows accurate temperature control of culture sensitive to a temperature, it is possible to uniformly set a temperature condition for a plurality of cultures.

Second Embodiment

Figure 5:
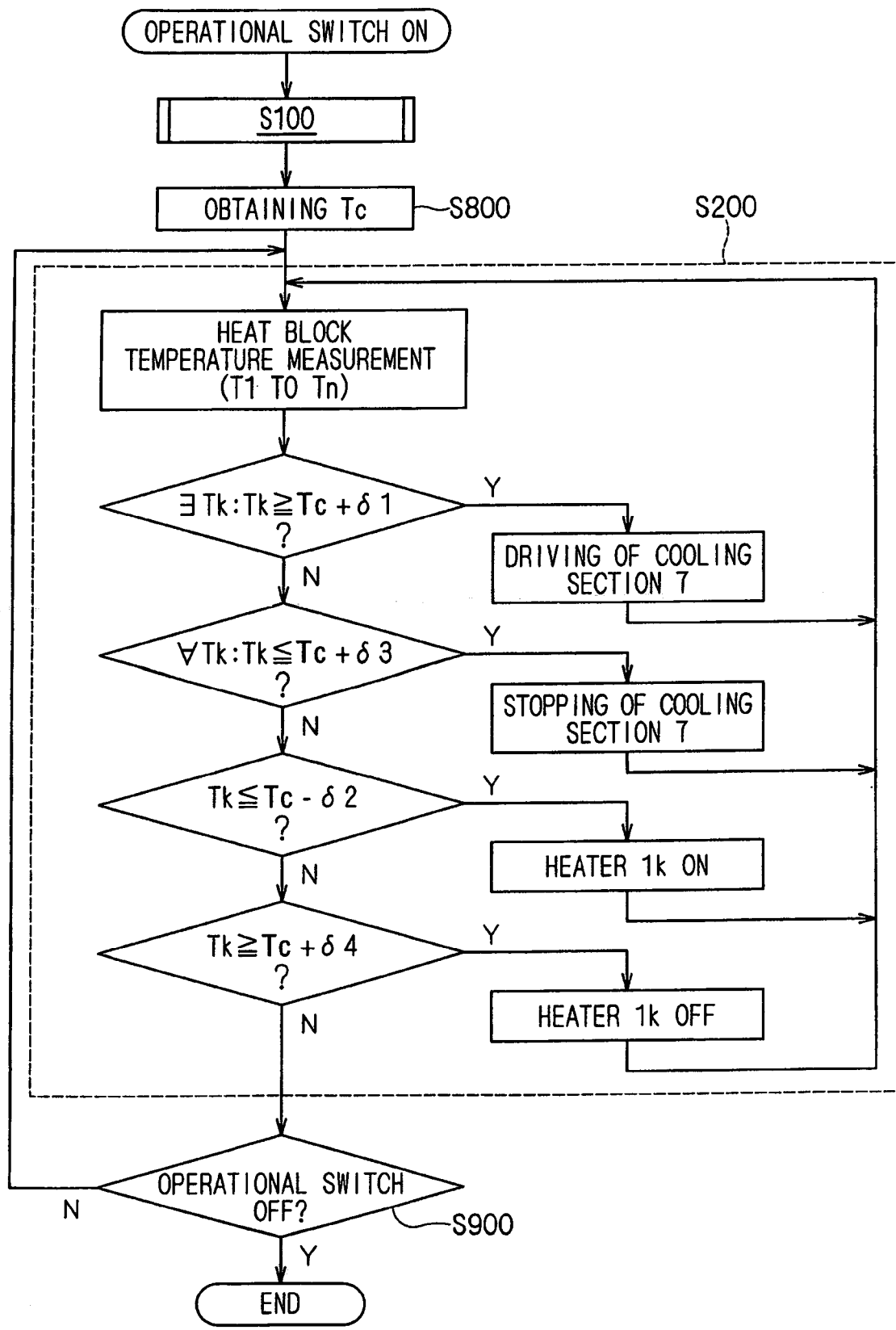
FIG. 5 is a flowchart exemplifying a temperature controlling method according to a second embodiment of the present invention.

FIG. 5 is a flowchart exemplifying the temperature controlling method according to the present invention. In the present embodiment, Steps S800 and S200 are executed in this order after execution of Step S100 of FIG. 4 until execution of Step S900.

Namely, when at least one temperature Tk is higher than the lower limit (Ts+δ3), all the temperatures T1 to Tn are lower than the upper limit (Ts+δ1), and any of the temperatures T1 to Tn is higher than the lower limit (Ts−δ2) and lower than the upper limit (Ts+δ4), the process proceeds to Step S800.

In Step S800, the target value Ts is calibrated to update to a new target value Tc according to the atmospheric temperature Ta of the temperature controller. Further, the process proceeds to Step S200.

Step S200 is a step where the target value Ts in Step S100 is changed to a target value Tc. With the atmospheric temperature taken into consideration in the temperature control, an effect on the cell temperature exerted by the atmospheric temperature Ta can be made small. Since the temperatures T1 to Tn have already been measured in Step S100, the process corresponding to Step S101 in Step S100 may be omitted in Step 200.

Third Embodiment

In above-mentioned Steps S103 and S105, since n temperatures are compared with the upper limit and the lower limit, the total of 2n of comparison operations are performed. However, once the maximum value M of the temperatures T1 to Tn is obtained, it is possible to perform only two comparison operations to obtain the effect shown in the first embodiment.

Figure 6:
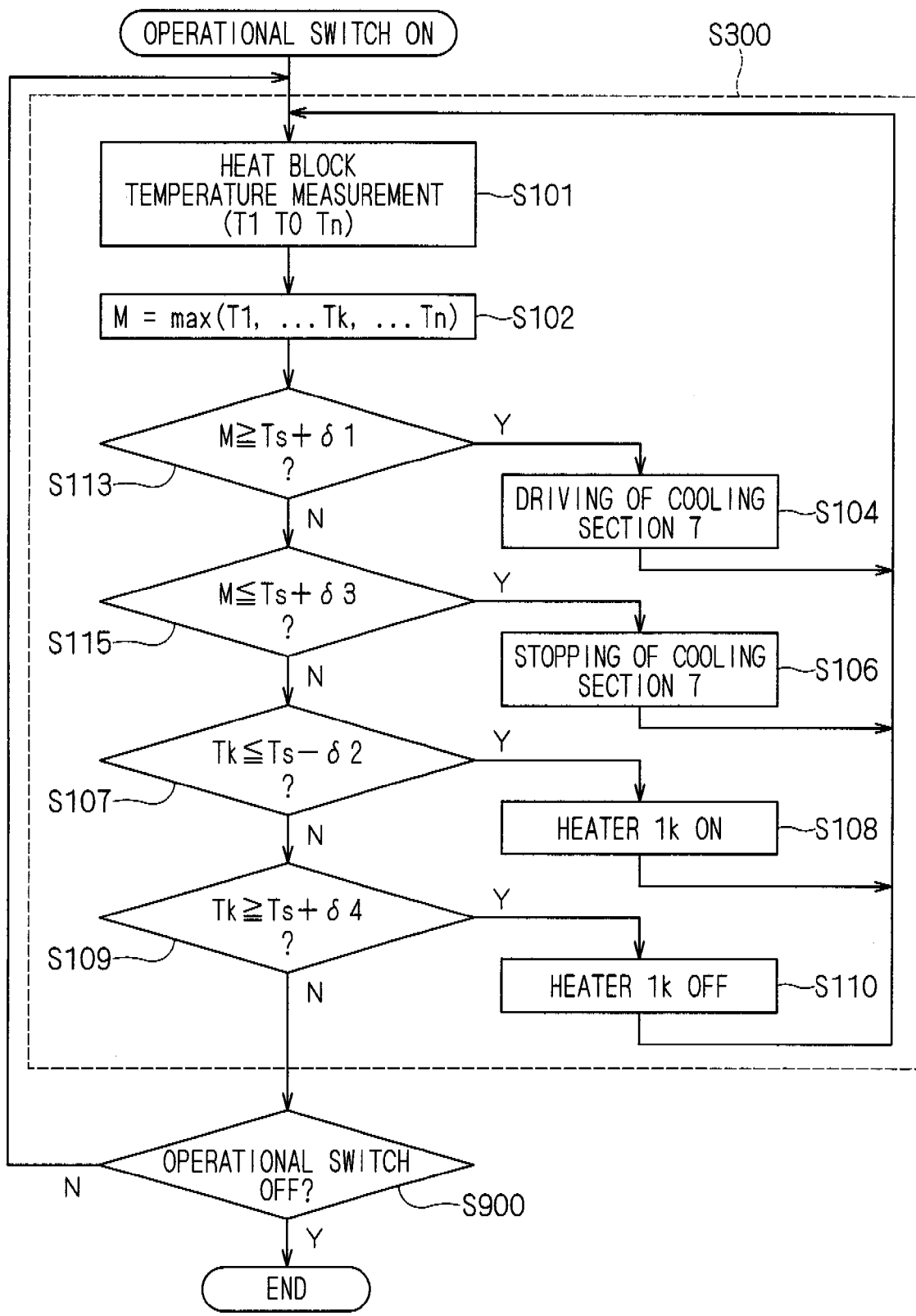
FIG. 6 is a flowchart exemplifying a temperature controlling method according to a third embodiment of the present invention.

FIG. 6 is a flowchart corresponding to FIG. 4, in which Step S100 has been replaced by Step S300. Step S300 has a configuration where Steps S103 and S105 in Step 5100 are respectively replaced by Steps S113 and S115, and a step S102 is added to between Step S101 and Step S113.

In Step S102, the maximum value M of the temperatures T1 to Tn is calculated. In FIG. 6, a symbol max represents the maximum value of a plurality of values in parentheses to the right of the symbol max.

In step S113, it is determined whether or not the maximum value M is not smaller than the prescribed upper limit (Ts+δ1). When this determination is affirmative, at least one heated cell 2 is present, and thus the process proceeds to Step S104.

When the maximum value M is smaller than the prescribed upper limit (Ts+δ1), all the temperatures T1 to Tn are smaller than the prescribed upper limit (Ts+δ1), so proceeding to Step S115 is done.

In step S115, it is determined whether or not the maximum value M is not larger than the prescribed lower limit (Ts+δ3). When this determination is affirmative, the cell temperatures of all the cells 2 have excessively decreased with respect to the target value, and the process thus proceeds to Step S106.

When the maximum value M is larger than the lower limit (Ts+δ3), proceeding to Step S107, or further to Step S109 is done, and each of the measured temperatures Tk is respectively compared with the prescribed lower limit (Ts−δ2) and upper limit (Ts+δ4).

Figure 7:
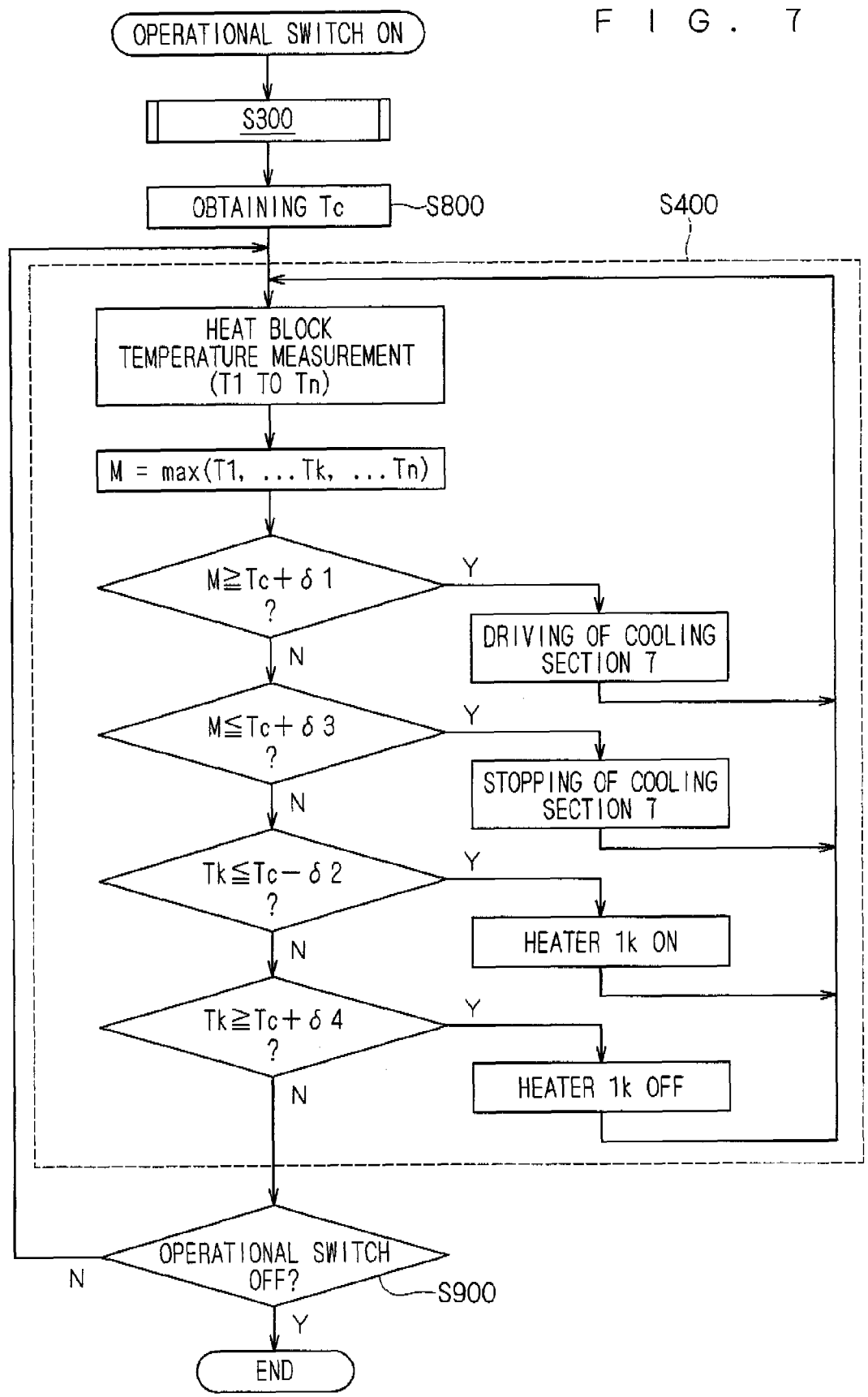
FIG. 7 is a flowchart exemplifying a temperature controlling method according to the third embodiment of the present invention.

FIG. 7 is a flowchart corresponding to FIG. 5, in which Steps S100 and S200 are replaced by Steps S300 and S400, respectively, and it is possible to obtain the effect shown in the second embodiment.

Step S400 is a step where the target value Ts is changed to a target value Tc with respect to Step S300. Since the temperatures T1 to Tn have already been measured in Step S300, the process corresponding to Steps S101 and S102 in Step S300 may be omitted in Step S400.

Naturally, Step S800 and Step S400 may be executed after execution of Step S100. In such a case, it is necessary to obtain the maximum value M in Step S400. Further, Step S800 and Step S200 may be executed after execution of Step S300.

Fourth Embodiment

Figure 8:
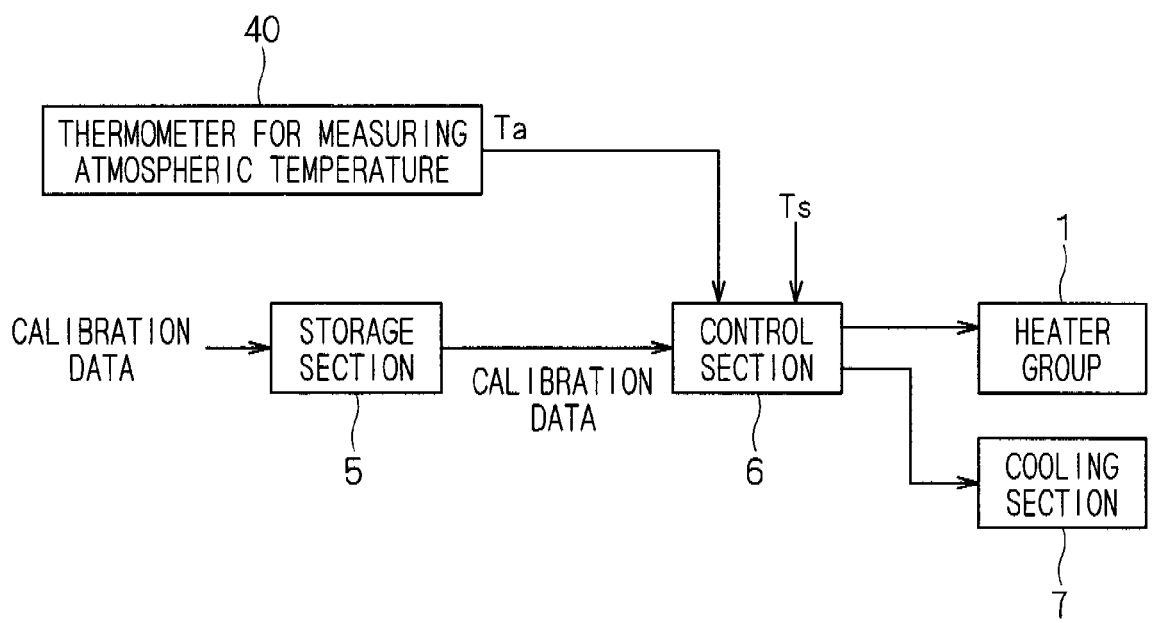
FIG. 8 is a block diagram exemplifying a configuration of a fourth embodiment of the present invention.

FIG. 8 is a block diagram, exemplifying a technique for correcting control by the heater group 1 and the cooling section 7 by means of the atmospheric temperature Ta, where operations of the first to third embodiments are accomplished. The temperature controller further includes a thermometer 40, a storage section 5, and a control section 6. The control section 6 controls the heater group 1 and the cooling section 7 according to the flowcharts shown in FIGS. 4 to 7. The thermometer 40 measures the atmospheric temperature Ta of circumstances under which the temperature controller has been set, and the storage section 5 storages calibration data.

The calibration data is obtained, for example, in the following manner. A cell temperature controlled by using Step S100 is previously set at each of different atmospheric temperatures Ta. The relation between the target value Ts of the heater temperature and the cell temperature at each of the atmospheric temperatures Ta is represented by a table, which is then adopted as calibration data.

The control section is provided with not only the target value Ts of the cell temperature but also with the atmospheric temperature Ta from the thermometer 40 and the calibration data from the storage section 5. According to the atmospheric temperature Ta, the control section 6 obtains a new target value Tc on the basis of the target value Ts of the cell temperature and the calibration data such that the cell temperature is the target value Ts. The control section 6 then executes Step S200 by using the target value Tc after update.

Figure 9:
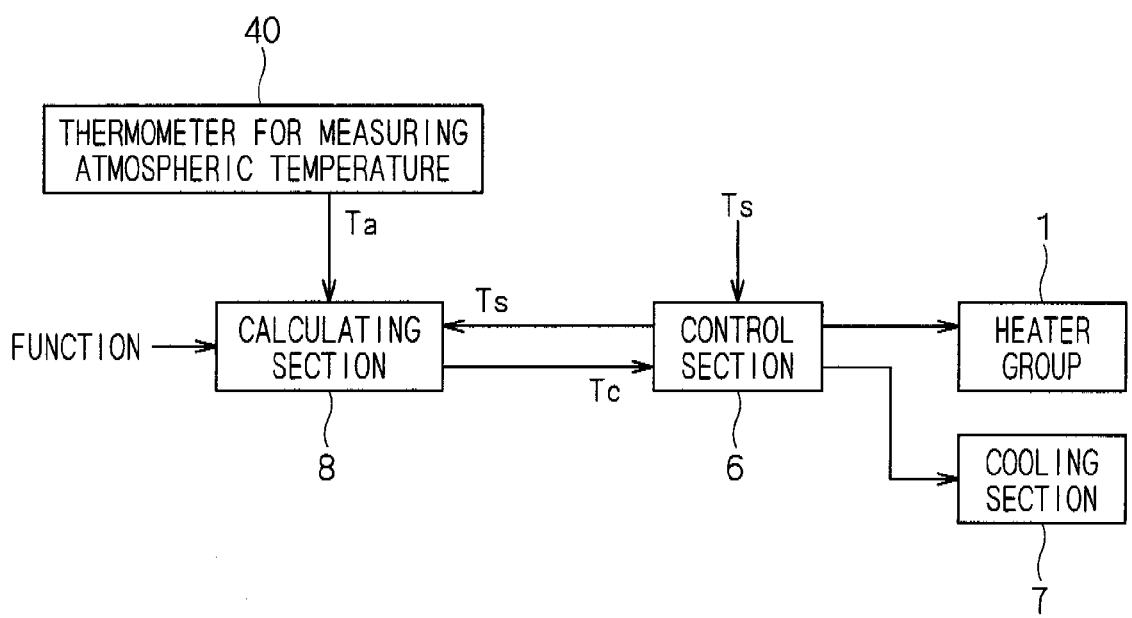
FIG. 9 is a block diagram exemplifying another configuration of the fourth embodiment of the present invention.

FIG. 9 is a block diagram exemplifying another technique for correcting the control by the heater group 1 and the cooling section 7 by means of the atmospheric temperature Ta. The temperature controller includes a calculating section 8 in place of the storage section 5.

The calculating section 8 is provided with a prescribed function, the atmospheric temperature Ta and the target value Ts. The target value Ts is, for example, provided from the control section 6.

The function is, for example, obtained as follows. A cell temperature controlled by using Step S100 or Step S300 is previously measured at each of different atmospheric temperatures Ta. The relation among the atmospheric temperature Ta, the target value Ts and the cell temperature is adopted as the function.

By using the function, the calculating section 8 obtains a new target value Tc from the atmospheric temperature Ta and the target value Ts such that the cell temperature is the target value Ts. By using the target value Tc after update, the control section 6 executes Step S200 or Step S400.

The foregoing temperature controller can be utilized not only in the case of culturing microorganisms or the like but also in the case of measuring an amount, effect, etc. of a chemical material by using microorganisms or the like as mediums, for example through the use of respiration activity of microorganisms or the like, or in a case where microorganisms or the like come into extinction.

The present invention was specifically described, but the above descriptions are exemplifications in all aspects and the present invention is not limited thereto. It is understood that innumerable modified examples which are not exemplified can be conceived without deviating from the range of the present invention.

What is claimed is:

1. A temperature controlling method, to control a temperature controller comprising:

a temperature-controlled object whose temperature is to be controlled;

heaters for heating a plurality of places of said temperature-controlled object; and a cooling section for cooling the whole of said temperature-controlled object, the method executing:

(a) a step of measuring temperatures of said plurality of places;

(b) a step of driving said cooling section when at least one of said temperatures of said places is not lower than a first upper limit;

(c) a step of selectively driving one of said heaters for heating one of said places when said temperature of the one of said places is not higher than a first lower limit;

(d) a step of not driving said cooling section when all of said temperatures of said places are not higher than a second lower limit; and (e) a step of not driving one of said heaters for heating one of said places when said temperature of the one of said places is not lower than a second upper limit.

2. The temperature controlling method according to claim 1, wherein
said second lower limit is lower than said first upper limit, and is a value obtained by adding a third positive value to a target value of a temperature of said temperature-controlled object, and
said second upper limit is higher than said first lower limit, and is a value obtained by adding a fourth positive value to said target value.

3. The temperature controlling method according to claim 2, further executing:
(f) a step of calibrating to update said target value to a new target value according to an atmospheric temperature of said temperature controller when at least one of said temperatures of said places is higher than said second lower limit, all of said temperatures of said places are lower than said first upper limit, and any of said temperatures of said places is higher than said first lower limit and lower than said second upper limit, and
again executing said steps (b) and (c) by using said target value updated in said step (f).

4. The temperature controlling method according to claim 3, again executing said steps (d) and (e) by using said target value updated in said step (f).

5. The temperature controlling method according to claim 1, wherein
said temperature-controlled object has a plurality of containers capable of housing cultures.

6. The temperature controlling method according to claim 5, wherein
said first upper limit is a value obtained by adding a first positive value to a target value of a temperature of said temperature-controlled object, and
said first lower limit is a value obtained by subtracting a second positive value from said target value.

7. The temperature controlling method according to claim 1, wherein
said first upper limit is a value obtained by adding a first positive value to a target value of a temperature of said temperature-controlled object, and
said first lower limit is a value obtained by subtracting a second positive value from said target value.

8. A temperature controller, comprising:
a housing section for housing a plurality of containers whose temperatures are to be controlled;
a cooling section for concurrently cooling all of said plurality containers housed in said housing section;
a plurality of heaters for selectively heating said plurality of containers;
a plurality of sensors for measuring temperatures of respective places heated by said plurality of heaters; and
a control section for controlling a drive of said cooling section on the basis of a target value of temperatures of said containers and on the basis of results of temperature measurement by said plurality of sensors, and for controlling a drive of said heaters on the basis of each said result of temperature measurement by said sensors such that
said cooling section is driven when at least one of said temperatures of said places is not lower than a first upper limit,
one of said heaters is selectively driven to heat one of said places when said temperature of the one of said places is not higher than a first lower limit,
said cooling section is not driven when all of said temperatures of said places are not higher than a second lower limit, and
one of said heaters is not driven when said temperature of one of said places is not lower than a second upper limit.

9. The temperature controller according to claim 8, further comprising:
a sensor for measuring an atmospheric temperature; and
a calculating section for updating said target value on the basis of said atmospheric temperature and said target value.

10. The temperature controller according to claim 8, further comprising:
a sensor for measuring an atmospheric temperature; and
a storage section for storing calibration data that provides a calibration value on the basis of said atmospheric temperature and said target value, wherein
said control section updates said target value with said calibration value on the basis of said calibration data, said atmospheric temperature and said target value.

* * * * *